United States Patent [19]

Pittet et al.

[11] Patent Number: 4,504,508
[45] Date of Patent: Mar. 12, 1985

[54] FLAVORING WITH PHENYLALKYL MERCAPTALS

[75] Inventors: Alan O. Pittet, Atlantic Highlands; Thomas F. Courtney, Jr., Oakhurst; Ranya Muralidhara, Fair Haven, all of N.J.

[73] Assignee: International Flavors & Fragrances Inc., New York, N.Y.

[21] Appl. No.: 602,513

[22] Filed: Apr. 20, 1984

Related U.S. Application Data

[63] Continuation-in-part of Ser. No. 541,151, Oct. 12, 1983.

[51] Int. Cl.³ .................... A23L 1/226; A23L 1/234
[52] U.S. Cl. ........................................ 426/535; 568/57
[58] Field of Search ..................... 426/535; 568/57

[56] References Cited

U.S. PATENT DOCUMENTS

| | | | |
|---|---|---|---|
| 1,696,419 | 12/1928 | Staudinger et al. | 426/535 X |
| 3,702,253 | 11/1972 | Winter et al. | 426/535 X |
| 3,968,264 | 7/1976 | Winter et al. | 426/535 |
| 4,200,660 | 4/1980 | Winter et al. | 426/535 |

Primary Examiner—Joseph Golian
Attorney, Agent, or Firm—Arthur L. Liberman

[57] ABSTRACT

Described are phenyl mercaptals defined according to the generic structure:

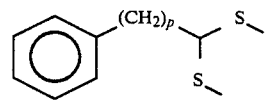

wherein p represents 0 or 1 and uses thereof in augmenting or enhancing the aroma or taste of foodstuffs.

8 Claims, 4 Drawing Figures

GLC PROFILE FOR EXAMPLE I
CRUDE

GLC PROFILE FOR EXAMPLE II.
CRUDE

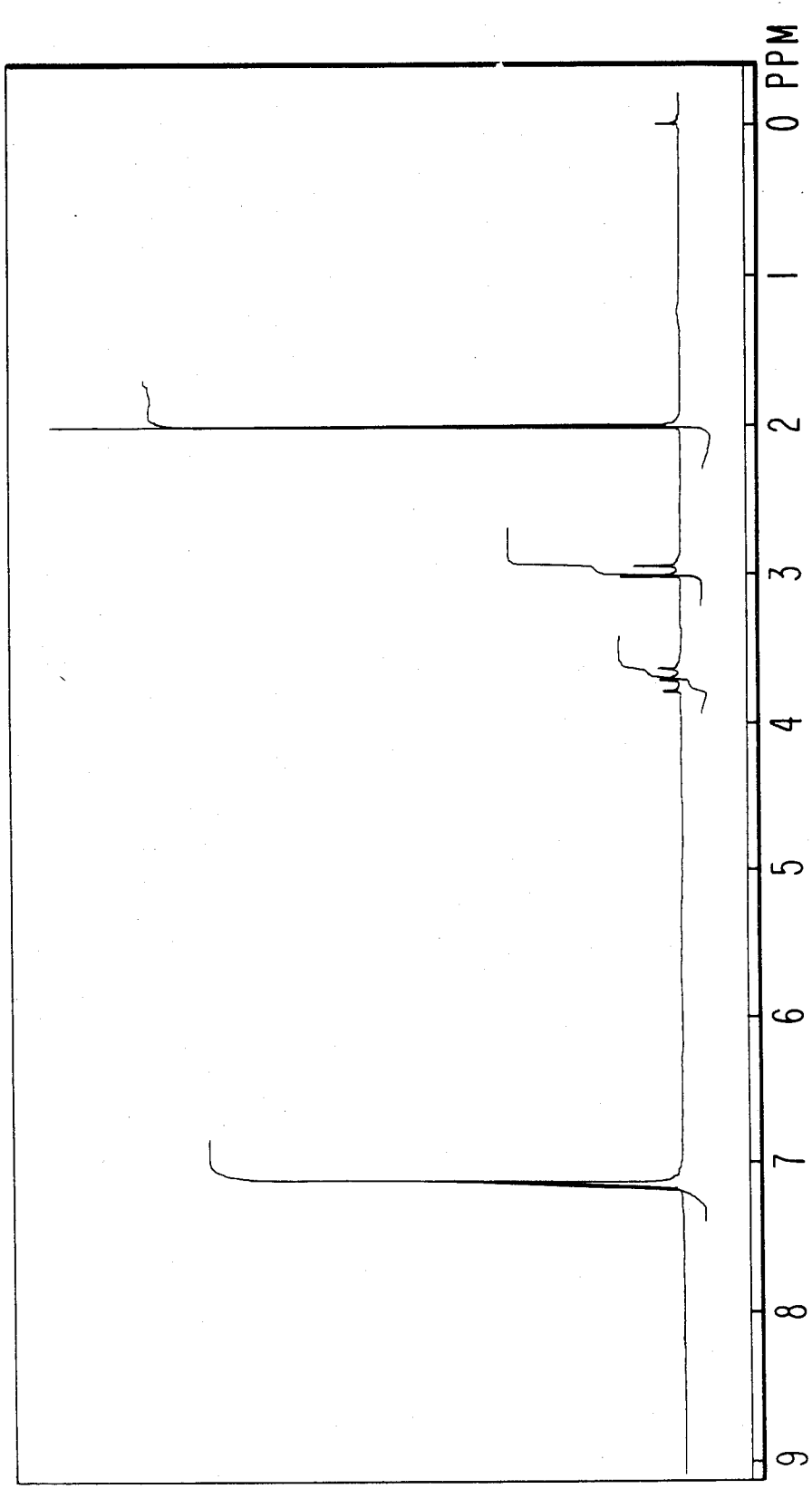

FLAVORING WITH PHENYLALKYL MERCAPTALS

This application is a continuation-in-part of application for United States Letters Patent, Ser. No. 541,151 filed on Oct. 12, 1983.

BACKGROUND OF THE INVENTION

This invention relates to phenyl mercaptals defined according to the structure:

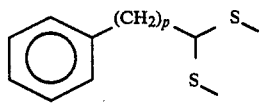

wherein p represents 0 or 1 and uses thereof in augmenting or enhancing the aroma or taste of foodstuffs, particularly roasted almond, roasted peanut, cocoa, sesame seed, peanut butter, chocolate and caramel flavored foodstuffs.

There has been considerable work performed relating to substances which can be used to impart (modify, augment or enhance) flavors to (or in) foodstuffs. These substances are used to diminish the use of natural materials some of which may be in short supply and to provide more uniform properties in the finished product.

Roasted, roasted peanut, peanut butter-like, floral and rosy aromas and roasted, roasted peanut, cocoa powder-like, peanut butter-like, floral and rosy taste nuances are particularly desirable for uses in many foodstuff flavors particularly in roasted almond, roasted peanut, cocoa, sesame seed, peanut butter, chocolate and caramel flavored foodstuffs.

Mercaptals of carbonyl derivatives are known in the prior art for augmenting or enhancing the aroma or taste of foodstuffs. Thus, mercaptals covered by the genus having the structure:

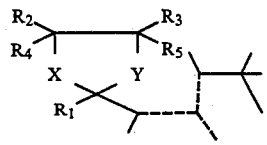

wherein $R_1$ represents $C_1$–$C_3$ lower alkyl; $R_2$, $R_3$, $R_4$ and $R_5$ represent the same or different hydrogen or $C_1$–$C_3$ lower alkyl; X and Y represent the same or different oxygen or sulfur; and one of the dashed lines represents a carbon-carbon double bond and the other of the dashed lines represent carbon-carbon single bonds are disclosed in U.S. Pat. No. 4,379,754 issued on Apr. 12, 1983 for use in augmenting or enhancing the aroma or taste of foodstuffs.

Many compounds in the prior art are disclosed for augmenting or enhancing onion flavors including providing lachrymatory effects (the effect obtained when eating a raw fresh green onion). Thus, U.S. Pat. No. 3,751,269 issued on Apr. 7, 1983 discloses onion flavoring compounds which provide such lachrymatory effects including thioalkanal-S-oxides and alkyl alkene thiosulfonates.

Black pepper flavor and aroma are provided in application for U.S. Letters Patent Ser. No. 774,056 filed on Mar. 3, 1977 (now abandoned).

Arctander, "Perfume and Flavor Chemicals (Aroma Chemicals)" Volume I at Monograph 272 discloses the organoleptic utilities of benzaldehyde ethyleneglycolacetal having the structure:

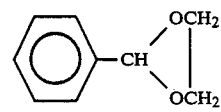

and at Monograph 274 discloses the organoleptic properties of benzaldehyde propyleneglycol acetal having the structure:

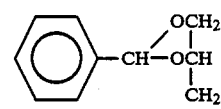

Arctander states that benzaldehyde propyleneglycol acetal is used in flavor compositions for imitation cherry, almond, nut, particularly where greater stability and lower volatility of the "bitter almond" theme is desirable but that the acetal itself is practically odorless "but will liberate benzaldehyde under influence of moisture (particularly in the presence of acid) and heat". Benzaldehyde propyleneglycol acetal is on the G.R.A.S. list as F.E.M.A. number 2130. Arctander further states that benzaldehyde ethyleneglycolacetal is suggested for use in flavor compositions where storage conditions favor a more stable form of benzaldehyde.

The compound defined according to the structure:

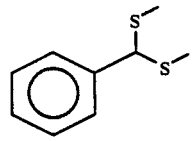

is known, but not for flavoring foodstuffs. Thus, U.S. Pat. No. 3,075,020 (Class 568 subclass 57) issued on Jan. 22, 1963 (Webb) sets forth the compound having the structure:

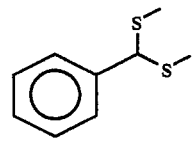

as an intermediate to make vulcanization accelerators and high pressure lubricants. Furthermore, the genus defined according to the structure:

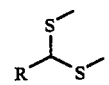

wherein R may be phenyl is disclosed in U.S. Pat. No. 2,864,739 issued Dec. 16, 1958 (Class 568 subclass 57) (Scott, et al.) as intermediates for production of insecticides.

Furthermore, the compound defined according to the structure:

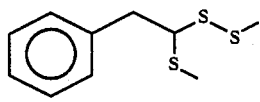

as disclosed by Dubs, et al. at Helv.Chim. Acta., Vol. 61, FASC. 7, (1978) at page 2354 (Formula le). Title of paper: "Investigation of the Head Space of Roasted Meat II, Syntheses of Substituted 2,4,5-Trithiahexanes.

Canadian Pat. No. 1,066,185 at Example 16 discloses a process for using the compound defined according to the structure:

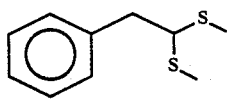

as an intermediate for making mercaptal-S-oxides.

Nothing in the prior art however discloses the phenyl mercaptals of our invention insofar as their organoleptic uses are concerned.

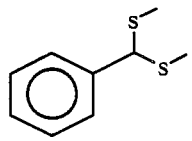

(conditions: Carbowax column programmed at 100°–220° C. at 8° C. per minute).

Figure 1:
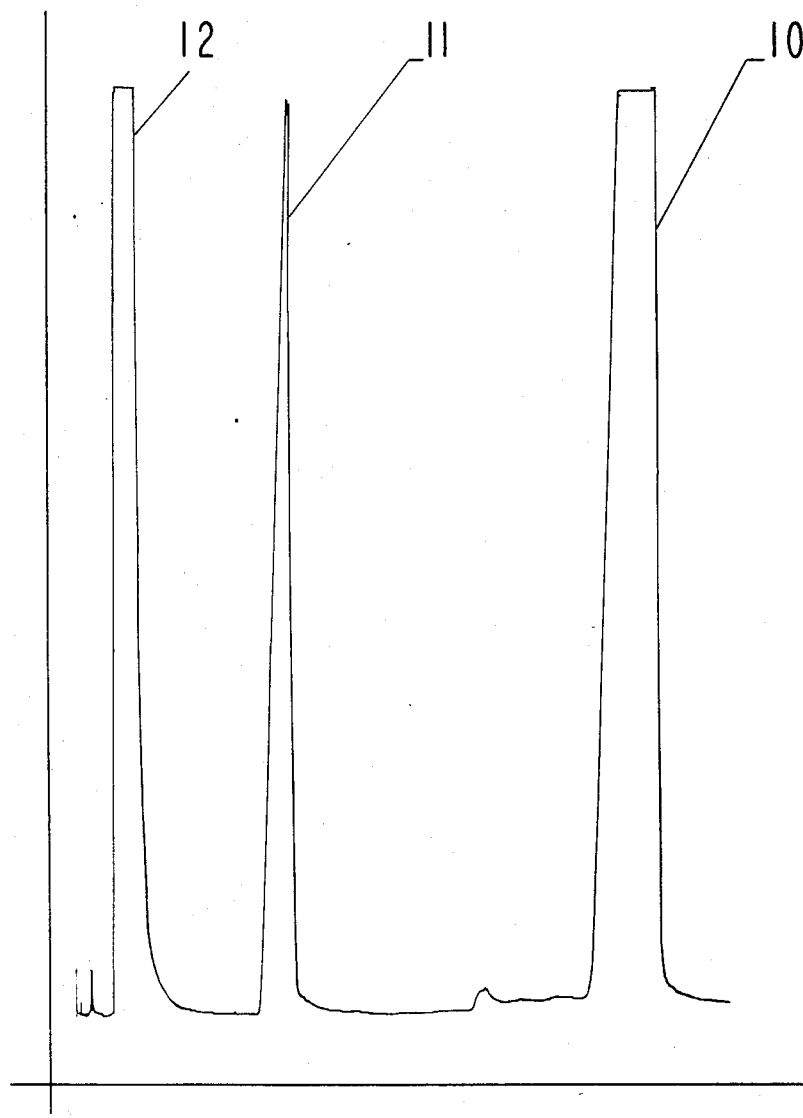
FIG. 1 is the GLC profile for the crude reaction product of Example I containing the compound having the structure.
Figure 2:
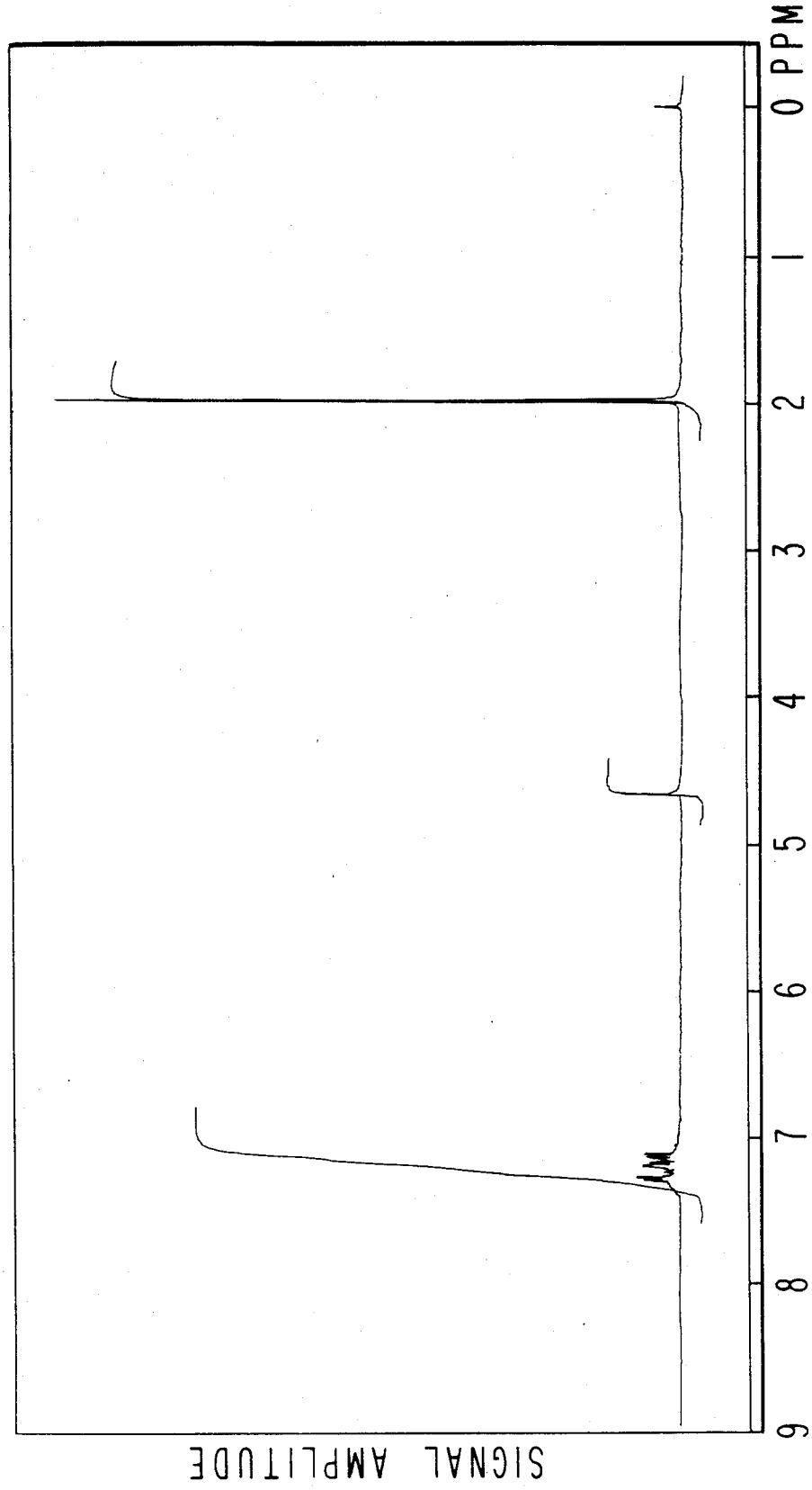

FIG. 2 is the NMR spectrum for peak "10" of the GLC profile of FIG. 1 for the compound having the structure:

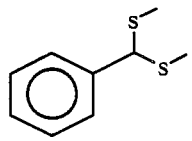

(conditions: Field strength: 100 MHz; Solvent: CFCl$_3$).

Figure 3:
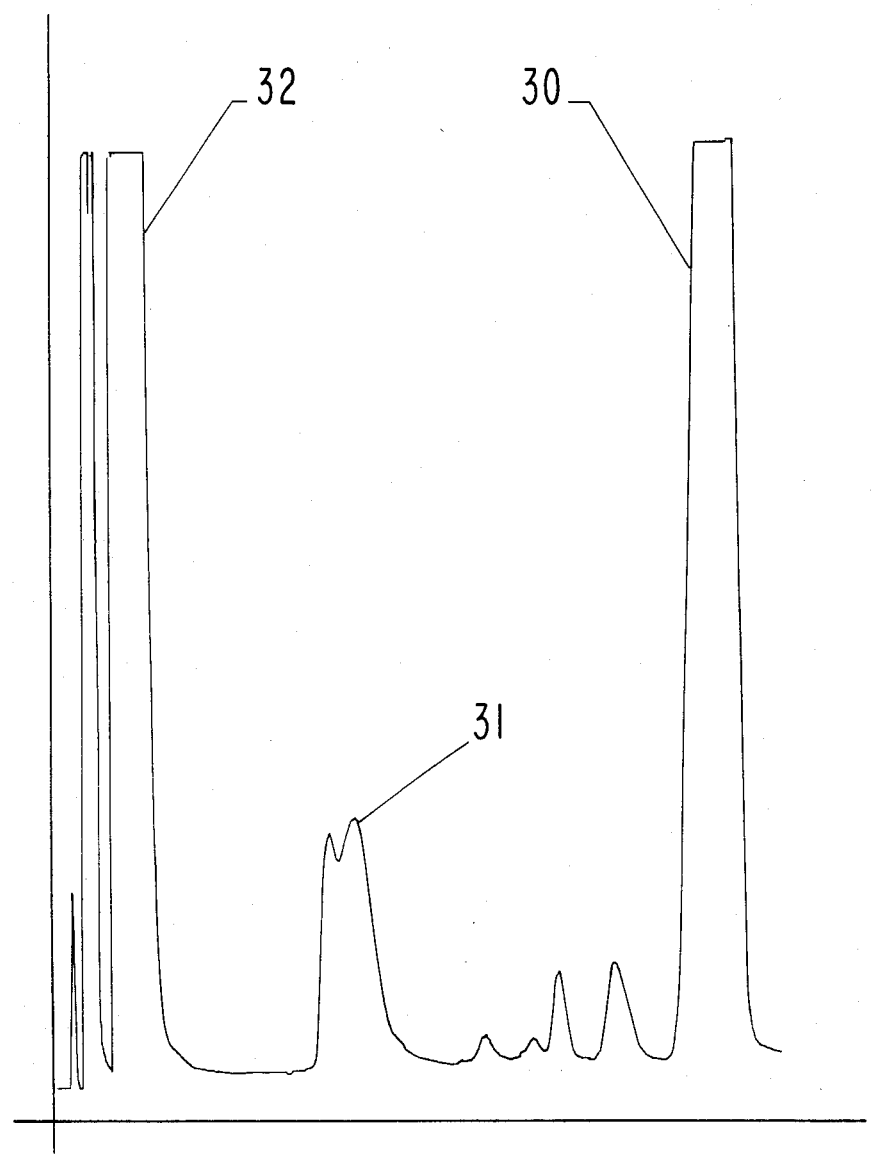

FIG. 3 is the GLC profile for the crude reaction product of Example II containing the compound having the structure:

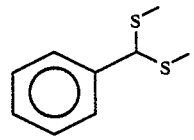

(conditions: 8'×0.25" carbowax column programmed at 100°–220° C. at 8° C. per minute).

FIG. 4 is the NMR spectrum for the peak indicated by reference numeral "30" of FIG. 3 containing the compound having the structure:

DETAILED DESCRIPTION OF THE DRAWINGS

FIG. 1, the GLC profile of the crude reaction product of Example I (conditions: Carbowax column programmed at 100°–220° C. at 8° C. per minute) shows three peaks, to wit:

(i) Peak "10" containing the compound having the structure:

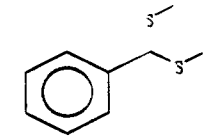

(ii) Peak "11" for benzaldehyde and Peak "12" for the cyclohexane reaction solvent.

FIG. 3 is the GLC profile for the crude reaction product of Example III (conditions: 8'×0.25" carbowax column programmed at 100°–220° C. at 8° C. per minute). Three major peaks are indicated in FIG. 3, to wit:

(i) Peak "30" for the compound having the structure:

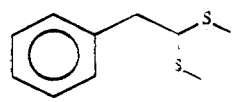

(ii) Peak "31" for phenyl acetaldehyde; and
(iii) Peak "32" for the cyclohexane reaction solvent.

THE INVENTION

The instant invention provides the genus defined according to the structure:

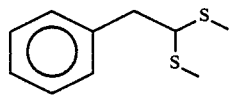

wherein p represents 0 or 1. These compounds hereinafter referred to as "phenyl mercaptals" are useful in augmenting or enhancing the aroma and/or taste of foodstuffs.

Briefly, our invention contemplates augmenting or enhancing the aroma or taste of roasted almond, roasted peanut, cocoa, sesame seed, peanut butter, chocolate and caramel flavored foodstuffs.

The compounds defined according to the genus:

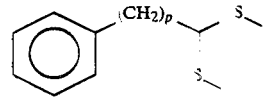

wherein p represents 0 or 1 augment or enhance roasted, roasted peanut, peanut butter-like, floral and rosy aroma nuances and roasted, roasted peanut, cocoa powder-like, peanut butter-like, floral and rosy taste nuances in foodstuffs as set forth, supra.

The phenyl mercaptals defined according to the structure:

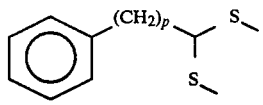

wherein p represents 0 or 1 may be produced by means of reacting methyl mercaptan with an aldehyde defined according to the structure:

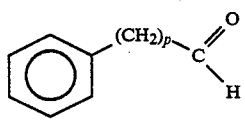

wherein p represents 0 or 1 in the presence of a protonic acid catalyst such as paratoluenesulfonic acid, xylene sulfonic acid, methane sulfonic acid, phosphoric acid and concentrated sulfuric acid. The reaction takes place in the presence of a solvent having a boiling point such that the reaction can proceed in a reasonable period of time, e.g. 1-12 hours, at atmospheric pressure or pressures somewhat greater than atmospheric pressure (up to about 10 atmospheres). The reaction temperature may vary from between about 70° C. up to about 140° C. Reaction temperatures greater than 140° C. give rise to unnecessary breakdown of reaction product. Reaction temperatures lower than 70° C. give rise to too long a period of time of reaction. The solvents utilized must be inert to the reaction product as well as inert to the reactants. The solvent utilized must also have a boiling point of between 70° C. and 140° C. since the reaction is to take place under reflux conditions. The reaction solvent must also be capable of being completely removed from the product on distillation in view of the fact that the reaction products are used as food flavors for internal consumption. Accordingly, suitable solvents are, for example, cyclohexane, cyclopentane, cyclooctane, 1-methylcyclohexane, 1,2-dimethylcyclohexane, 1,2,4-trimethylcyclohexane, 2-ethyltetrahydrofuran, 2,5-dimethyltetrahydrofuran and the like.

The mole ratio of the aldehyde defined according to the structure:

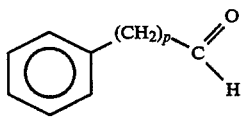

to methyl mercaptan is preferably about 1:2 since two (2) moles of methyl mercaptan are desired to be reacted with one mole of the aldehyde defined according to the structure:

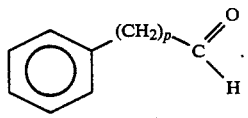

Accordingly, the reaction used in preparing the compound useful in our invention is as follows:

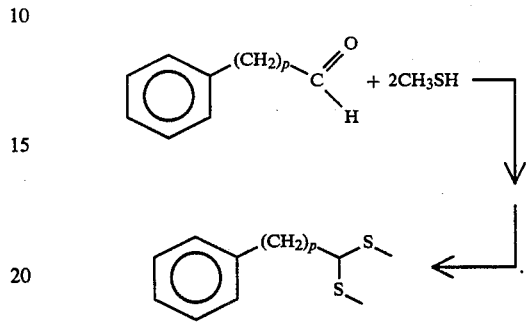

At the end of the reaction the reaction product is extracted from the reaction mass or the reaction mass is washed, for example, with saturated sodium chloride. The reaction product is then distilled, preferably by means of vacuum distillation using a fractionation column.

Examples of the products of our invention and their organoleptic properties are as follows:

TABLE I

| Structure of Compound | Organoleptic Properties |
| --- | --- |
|  | A roasted and roasted peanut aroma with roasted, roasted peanut and cocoa powder taste nuances at 0.01 ppm. |
|  | A roasted, roasted peanut, peanut butter-like, floral and rosy aroma and taste profile at 0.01 ppm. |
|  | Is useful in roasted almond, roasted peanut and cocoa flavors. |
|  | Is useful in roasted peanut, roasted almond, sesame seed, peanut butter, cocoa, chocolate and caramel flavored foodstuffs. |

When one of the phenyl mercaptals of our invention is used as a food flavor adjuvant, the nature of the co-ingredients included with one of the phenyl mercaptals in formulating the product composition will also serve to alter, modify, augment or enhance the organoleptic characteristics of the ultimate foodstuff treated therewith.

As used herein in regard to flavors, the terms "alter", "modify" and "augment" in their various forms mean "supplying or imparting flavor character or note to otherwise bland, relatively tasteless substances or augmenting the existing flavor characteristic where a natural flavor is deficient in some regard or supplementing the existing flavor impression to modify its quality, character or taste".

The term "enhance" is used herein to mean the intensification of a flavor or aroma characteristic or note without the modification of the quality thereof. Thus, "enhancement" of a flavor or aroma means that the enhancement agent does not add any additional flavor note.

As used herein, the term "foodstuff" includes both solid and liquid ingestible materials which usually do, but need not, have nutritional value. Thus, foodstuffs include soups, convenience foods, beverages, dairy products, candies, vegetables, cereals, soft drinks, snacks and the like.

Substances suitable for use herein as co-ingredients or flavoring adjuvants are well known in the art for such use, being extensively described in the relevant literature. It is a requirement that any such material be "ingestibly" acceptable and thus non-toxic and otherwise non-deleterious particularly from an organoleptic standpoint whereby the ultimate flavor and/or aroma of the consumable material used is not caused to have unacceptable aroma and taste nuances. Such materials may in general be characterized as flavoring adjuvants or vehicles comprising broadly stabilizers, thickeners, surface active agents, conditioners, other flavorants and flavor intensifiers.

Stabilizer compounds include preservatives, e.g. sodium chloride; antioxidants, e.g. calcium and sodium ascorbate, ascorbic acid, butylated hydroxy-anisole (mixture of 2- and 3-tertiary-butyl-4-hydroxy-anisole), butylated hydroxy toluene (2,6-di-tertiary-butyl-4-methyl phenol), propyl gallate and the like and sequestrants, e.g. citric acid.

Thickener compounds include carriers, binders, protective colloids, suspending agents, emulsifiers and the like, e.g. agar agar, carrageenan; cellulose and cellulose derivatives such as carboxymethyl cellulose and methyl cellulose; natural and synthetic gums such as gum arabic, gum tragacanth; gelatin, proteinaceous materials; lipids; carbohydrates; starches, pectins and emulsifiers, e.g. mono- and diglycerides of fatty acids, skim mild powder, hexoses, pentoses, disaccharides, e.g. sucrose, corn syrup and the like.

Surface active agents include emulsifying agents, e.g. fatty acids such as capric acid, caprylic acid, palmitic acid, myristic acid and the like, mono- and diglycerides of fatty acids, lecithin, defoaming and flavor-dispersing agents such as sorbitan monostearate, potassium stearate, hydrogenated tallow alcohol and the like.

Conditioners include compounds such as bleaching and maturing agents, e.g. benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g. sodium acetate, ammonium bicarbonate, ammonium phosphate, citric acid, lactic acid, vinegar and the like; colorants, e.g. carminic acid, cochineal, tumeric and curcuma and the like; firming agents such as aluminum sodium sulfate, calcium chloride and calcium gluconate; texturizers, anticaking agents, e.g. aluminum calcium sulfate and tribasic calcium phosphate, enzymes; yeast foods, e.g. calcium lactate and calcium sulfate; nutrient supplements, e.g. iron salts such as ferric phosphate, ferrous gluconate and the like, riboflavin, vitamins, zinc sources such as zinc chloride, zinc sulfate and the like.

Other flavorants and flavor intensifiers include organic acids, e.g. acetic acid, formic acid, 2-hexenoic acid, benzoic acid, n-butyric acid, caproic acid, caprylic acid, cinnamic acid, isobutyric acid, isovaleric acid, alpha-methyl-butyric acid, propionic acid, valeric acid, 2-methyl-2-pentenoic acid, and 2-methyl-3-pentenoic acid; ketones and aldehyde, e.g. acetaldehyde, acetophenone, acetone, acetyl methyl carbinol, acrolein, n-butanal, crotonal, diacetyl, 2-methyl butanal, beta,-beta-dimethylacrolein, methyl-n-amyl ketone, n-hexenal, 2-hexenal, isopentanal, hydrocinnamic aldehyde, cis-3-hexenal, 2-heptanal, nonyl aldehyde, 4-(p-hydroxyphenyl)-2-butanone, alpha-ionone, beta-ionone, methyl-3-butanone, benzaldehyde, damascone, damascenone, acetophenone, 2-heptanone, o-hydroxyacetophenone, 2-methyl-2-hepten-6-one, 2-octanone, 2-undecanone, 3-phenyl-4-pentenal, 2-phenyl-2-hexenal, 2-phenyl-2-pentenal, furfural, 5-methyl furfural, cinnamaldehyde, beta-cyclohomocitral, 2-pentanone, 2-pentenal and propanal; alcohols such as 1-butanol, benzyl alcohol, 1-borneol, trans-2-buten-1-ol, ethanol, geraniol, 1-hexanal, 2-heptanol, trans-2-hexenol-1, cis-3-hexen-1-ol, 3-methyl-3-buten-1-ol, 1-pentanol, 1penten-3-ol, p-hydroxyphenyl-2-ethanol, isoamyl alcohol, isofenchyl alcohol, phenyl-2-ethanol, alpha-terpineol, cis-terpineol hydrate, eugenol, linalool, 2-heptanol, acetoin; esters such as butyl acetate, ethyl acetate, ethyl acetoacetate, ethyl benzoate, ethyl butyrate, ethyl caprate, ethyl caproate, ethyl caprylate, ethyl cinnamate, ethyl crotonate, ethyl formate, ethyl isobutyrate, ethyl isovalerate, ethyl laurate, ethyl myristate, ethyl alpha-methyl-butyrate, ethyl propionate, ethyl salicylate, trans-2-hexenyl acetate, hexyl acetate, 2-hexenyl butyrate, hexyl butyrate, isoamyl acetate, isopropyl butyrate, methyl acetate, methyl butyrate, methyl caproate, methyl isobutyrate, alpha-methylphenylglycidate, ethyl succinate, isobutyl cinnamate, cinnamyl formate, methyl cinnamate and terpenyl acetate; hydrocarbons such as dimethyl naphthalene, dodecane, methyl diphenyl, methyl naphthalene, myrcene, naphthalene, octadecane, tetradecane, tetramethyl naphthalene, tridecane, trimethyl naphthalene, undecane, caryophyllene, 1-phellandrene, p-cymeme, 1-alpha-pinene, beta-pinene, dihydrocarveol; pyrazines such as 2,3-dimethylpryazine, 2,5-dimethylpyrazine, 2,6-dimethylpyrazine, 3-ethyl-2,5-dimethylpyrazine, 2-ethyl-3,5,6-trimethylpyrazine, 3-isoamyl-2,5-dimethylpyrazine, 5-isoamyl-2,3-dimethylpyrazine, 2-isoamyl-3,5,6-trimethylpyrazine, isopropyl dimethylpyrazine, methyl ethylpyrazine, tetramethylpyrazine, trimethyl-pyrazine; essential oils such as jasmine absolute, cassia oil, cinnamon bark oil, black pepper oleoresin, oil of black pepper, rose absolute, orris absolute, oil of cubeb, oil of coriander, oil of pimento leaf, oil of patchouli, oil of nutmeg, lemon essential oil, safran oil, Bulgarian rose oil, capsicum, yara yara and vanilla; lactones such as gamma-nonalactone; sulfides, e.g. allyl propenyl disulfide, dipropyl disulfide, dipropyl trisulfide, diallyl disulfide, diallyl trisulfide, 2-methyl-3-furyl methyl sulfide and bis(2-methyl-3-furyl)disulfide and other materials such as maltol, acetoin, acetals (e.g. 1,1-diethoxyethane, 1,1-dimethoxyethane, dimethoxymethane, 1-acetoxy-1-ethoxyethane and 1-acetoxy-1-methoxyethane), piperine, chavicine, piperidine, 2,5-dimethyl-3-acetyl furan, 2,5-dimethyl-3-acetyl thiophene and reaction products such as the reaction products described in U.S. Pat. Nos. 3,394,015, 3,394,016, 3,394,017, 3,682,692, 3,782,973 and 4,045,587, the disclosures of which are incorporated by reference herein.

The specific flavor adjuvants selected for use may be either solid or liquid depending upon the desired physical form of the ultimate produce, i.e. foodstuff, whether simulated or natural, and should, in any event, (i) be organoleptically compatible with one of the phenyl mercaptals of our invention by not covering or spoiling the organoleptic properties (aroma or taste) thereof; (ii) be nonreactive with the phenyl mercaptals of our invention and (iii) be capable of providing an environment in which one of the phenyl mercaptals of our invention can be dispersed or admixed to provide a homogeneous medium. In addition, selection of one or more flavoring adjuvants, as well as the quantities thereof will depend upon the precise organoleptic character desired in the finished product. Thus, in the case of flavoring compositions, ingredient selection will vary in accordance with the foodstuff to which the flavor and/or aroma are to be imparted, modified, altered or enhanced. In contradistinction, in the preparation of solid products, e.g. simulated foodstuffs, ingredients capable of providing normally solid compositions should be selected such as various cellulose derivatives.

As will be appreciated by those skilled in the art, the amount of one of the phenyl mercaptals employed in a particular instance can vary over a relatively wide range, depending upon the desired organoleptic effects to be achieved. Thus, correspondingly greater amounts would be necessary in those instances wherein the ultimate food composition to be flavored is relatively bland to the taste, whereas relatively minor quantities may suffice for purposes of enhancing the composition merely deficient in natural flavor or aroma. The primary requirement is that the amount selected to be effective, i.e. sufficient to alter, modify or enhance the organoleptic characteristics of the parent composition, whether foodstuff per se, chewing gum per se, medicinal product per se, toothpaste per se, or flavoring composition.

The use of insufficient quantities of one of the phenyl mercaptals will, of course, substantially vitiate any possibility of obtaining the desired results while excess quantities prove needlessly costly and, in extreme case, may disrupt the flavor-aroma balance, thus proving self-defeating. Accordingly, the terminology "effective amount" and "sufficient amount" is to be accorded a significance in the context of the present invention consistent with the obtention of desired flavoring effects.

Thus, and with respect to ultimate food compositions, chewing gum compositions, medicinal product compositions and toothpaste compositions, it is found that quantities of one of the phenyl mercaptals ranging from a small but effective amount, e.g., 0.005 ppm up to about 50 parts per million based on total composition, are suitable. Concentrations in excess of the maximum quantity stated are not normally recommended, since they fail to provide commensurate enhancement of organoleptic properties. In those instances wherein one of the phenyl mercaptals of our invention is added to the foodstuff as an integral component of a flavoring composition, it is, of course, essential that the total quantity of flavoring composition employed be sufficient to yield an effective phenyl mercaptals concentration in the foodstuff product.

Food flavoring compositions prepared in accordance with the present invention preferably contain one of the phenyl mercaptals in concentrations ranging from about 0.1% up to about 15% by weight based on the total weight of the said flavoring composition.

The composition described herein can be prepared according to conventional techniques well known as typified by meat pie crust batters and proteinaceous drinks and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing one of the phenyl mercaptals with, for example, gum arabic, gum tragacanth, carrageenan and the like, and thereafter spray-drying the resultant mixture whereby to obtain the particulate solid product. Pre-prepared flavor mixes in powder form, e.g. onion-flavored powder mix, are obtained by mixing the dried solid components, e.g. starch, sugar and the like, and one of the phenyl mercaptals of our invention in a dry blender until the requisite degree of uniformity is achieved.

It is presently preferred to combine with one of the phenyl mercaptals of our invention, the following adjuvants:

Oil of cubeb;
Phellandrene;
Oil of coriander;
Oil of pimento leaf;
Oil of patchouli;
Alpha pinene;
Beta-pinene;
Beta-caryophyllene;
Dihydrocarveol;
Piperonal;
Piperine;
Oil of black pepper;
Black pepper oleoresin;
Capsicum;
Oil of nutmeg;
Bis(2-methyl-3-furyl)disulfide;
Reaction products which produce meat flavors such as the reaction product of hydrogen sulfide and 2- or 5-monoalkyl and 2,5-dialkyl-4-hydroxy-2,3-dihydrofuran-3-ones;
Diallyl trisulfide;
Propyl propenyl trisulfide;
Propyl propenyl disulfide;
Propyl allyl disulfide;
Propyl allyl trisulfide;
1-propenyl allyl trisulfide;
Di(1-propenyl)disulfide;
Di(1-propenyl)trisulfide;
Thioethanal-S-oxide;
Propyl propene thiosulfonate;
Thiobutanal-S-oxide;
Thiohexanal-S-oxide;
Propyl propane thiosulfonate;
Propyl propenyl thiosulfonate; 4-Terpinenol propionate;
The reaction product of hydrolyzed vegetable protein, cysteine and thiamine as described in U.S. Pat. No. 3,394,015, the specification of which is incorporated by reference herein.

The following examples serve to illustrate the utility and process for preparing the phenyl mercaptals of our invention. It will be understood that these examples are illustrative and the invention is to be considered restricted thereto only as indicated in the appended claims.

All parts and percentages given herein are by weight unless otherwise specified.

EXAMPLE I

Preparation of the Dimethyl Mercaptal of Benzaldehyde

Reaction:

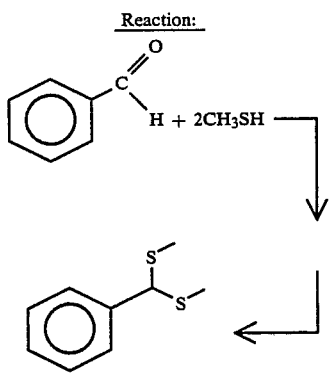

Into a 500 ml reaction flask equipped with reflux condenser, thermometer and stirring apparatus and heating mantle is placed 0.5 grams of paratoluenesulfonic acid, 21 grams of benzaldehyde and 100 ml cyclohexane. With stirring over a period of one hour, 10 grams of methyl mercaptan is bubbled into the reaction mass. The reaction mass is then stirred for a period of eight hours and then refluxed for an additional period of eight hours. The reaction mass is then cooled and transferred to a separatory funnel. The resulting reaction mass is then washed with one 50 ml portion of saturated sodium chloride solution, dried over anhydrous sodium sulfate and filtered. The resulting filtrate is distilled on a micro vigreux column yielding the compound having the structure:

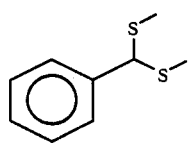

FIG. 1 is the GLC profile for the crude reaction product containing the compound having the structure:

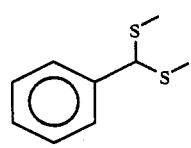

The peak indicated by reference numeral "10" is the peak for the compound having the structure:

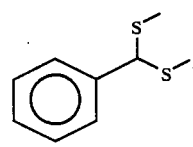

The peak indicated by reference numeral "11" is the peak for benzaldehyde. The peak indicated by reference numeral "12" is the peak for cyclohexane.

The conditions for operation of the GLC apparatus are: Carbowax column programmed at 100°-220° C. at 8° C. per minute.

The resulting product has a roasted and roasted peanut aroma with roasted, roasted peanut and cocoa powder nuances at 0.01 ppm.

FIG. 2 is the NMR spectrum for the compound having the structure:

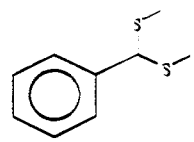

(conditions: Field strength: 100 MHz: Solvent: CFCl₃),

EXAMPLE II

Preparation of Dimethyl Mercaptal of Phenyl Acetaldehyde

Reaction:

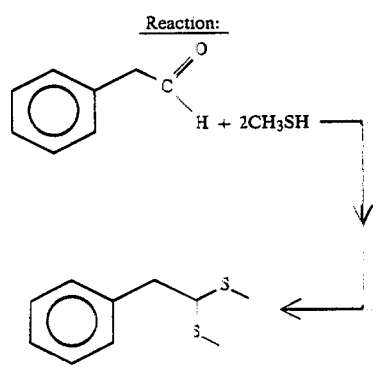

Into a 500 ml reaction flask equipped with stirrer, reflux condenser, thermometer and heating mantle is placed 20 grams of phenyl acetaldehyde, 200 ml cyclohexane and 0.5 grams of paratoluenesulfonic acid. Over a period of one hour, 10 grams of methyl mercaptan is bubbled into the reaction mass with stirring maintaining the reaction temperature at room temperature. The reaction mass is then stirred for a period of eight hours, after which time, it is heated to reflux and refluxed for a period of eight hours.

The reaction mass is then cooled and transferred to a separatory funnel. The resulting reaction mass is washed with 150 ml portion of saturated sodium chloride solution, dried over anhydrous sodium sulfate and filtered. The resulting filtrate is distilled on micro vigreux column.

FIG. 3 is the GLC profile for the crude reaction product containing the compound having the structure:

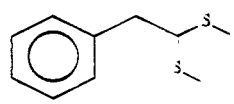

(conditions: 8'×0.25" carbowax column programmed at 100°-220° C. at 8° C. per minute). The peak indicated by reference numeral "30" is the peak for the compound having the structure:

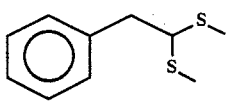

The peak indicated by reference numeral "31" is the peak for phenyl acetaldehyde. The peak indicated by reference numeral "32" is the peak for cyclohexane.

FIG. 4 is the NMR spectrum for the compound having the structure:

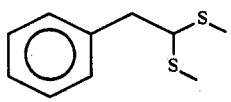

(conditions: Field strength: 100 MHz; Solvent: CFCl₃).

The resulting product has an intense roasted, roasted peanut, peanut butter-like, floral and rosy aroma and taste profile at 0.01 ppm causing it to be useful in roasted peanut, roasted almond, sesame seed, peanut butter, cocoa, chocolate and caramel flavors.

EXAMPLE III

Peanut Butter Flavor Enhancer

The following peanut flavor is produced:

| Ingredients | Parts by Weight |
| --- | --- |
| Compound prepared according to Example I. | 8.0 |
| Tetramethylpyrazine | 4.0 |
| 2-Acetyl-3,5-dimethyl pyrazine | 4.0 |
| 2,3,5-trimethyl pyrazine | 7.0 |

The resultant peanut flavor is added at the rate of 0.04 ppm to SKIPPY ® peanut butter. The resultant peanut butter has a more natural long-lasting natural freshly roasted peanut aroma and taste flavor (for a period of five weeks while normally refrigerated). The same result occurs when the compound having the structure:

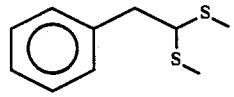

replaces the compound having the structure:

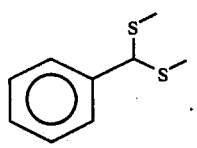

EXAMPLE IV

The following base cocoa flavor is prepared by admixing the following ingredients:

| Ingredients | Parts by Weight |
| --- | --- |
| Vanillin | 60.2 |
| Amylphenyl acetate | 45.0 |
| Benzylbutyrate | 4.5 |
| Veratraldehyde | 5.2 |
| Maltol | 3.2 |
| Ethyl maltol | 1.2 |
| Propyleneglycol | 560.0 |

To 1 gram of this base cocoa flavor, 3 mg of 5-methyl-2-phenyl-2-hexenal and 2 mg of the compound having the structure:

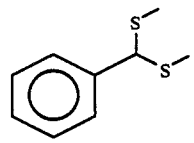

is added. The addition of the compound having the structure:

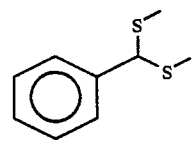

alters the imitation cocoa flavor to provide a more natural cocoa flavor and impart a character of a "nutty chocolate". When the compound having the structure:

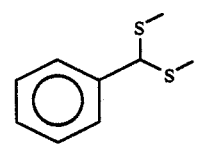

is replaced by the compound having the structure:

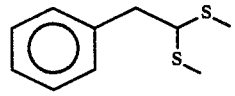

and a more intensified nutty, cocoa effect is created.

EXAMPLE V

A flavor composition is prepared by combining the following materials:

| Ingredients | Parts by Weight |
| --- | --- |
| 2-Methyl pyrazine | 1.5 |
| 2,3-Dimethyl pyrazine | 0.5 |
| 2-Ethyl-5-methyl pyrazine | 0.5 |
| 2,3,5-Trimethyl pyrazine | 1.0 |
| 2,5-Dimethyl pyrazine | 1.0 |
| 2-Ethyl-3,5,6-trimethyl pyrazine | 0.5 |
| The compound having structure: | 0.02 |

| Ingredients | Parts by Weight |
|---|---|
| 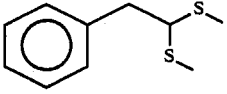 | |

The resulting mixture is gradually added to a chocolate liquor produced from Haiti cocoa beans. While the Haiti bean liquor has only a weak flavor, the addition of the foregoing mixture to a kilogram of the liquid gives an optimal flavor improvement particularly due to the compound having the structure:

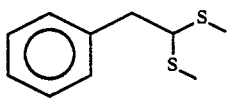

This addition gives such excellent chocolate flavor that the liquid compares favorably with liquors obtained from the highest quality Java or Ceylon (Sri Lanka) beans.

EXAMPLE VI

A chocolate flavored custard pudding mix is prepared with the following ingredients:

| Ingredients | Parts by Weight |
|---|---|
| Granulated sugar | 53 lbs. |
| Corn starch | 22 lbs. |
| Tapioca starch | 6 lbs. |
| Cocoa powder | 18 lbs. |
| Salt | 1 lb. |
| Vanillin | 2 ozs. |

After thorough mixing, the batch is packaged in individual units of 4 ounces each.

A first pudding is prepared by combining a unit of powder with one pint of milk. The pudding so obtained has a cocoa flavor which is somewhat harsh and thin. To a second 4 ounce unit of powder is added 0.4 mg of the compound having the structure:

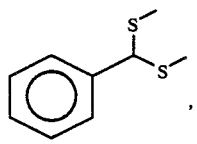

and a custard pudding is prepared from this by cooking the powder with a pint of milk. The second pudding has a fuller, richer cocoa flavor.

EXAMPLE VII

A commercial chocolate cake mix is made into a batter and baked according to the manufacturer's directions. A cake having a good crumb is obtained but the chocolate flavor is somewhat harsh and flat.

A second mix is prepared as above according to the directions and subsequently baked. Prior to baking, however, 30 mg of the flavor of Example V is added to the batter. A cake having a good crumb is obtained and the chocolate flavor is full and rounded.

What is claimed is:

1. A process for augmenting or enhancing the aroma or taste of a foodstuff comprising the step of intimately admixing with said foodstuff 0.005 ppm up to about 50 ppm of at least one compound defined according to the structure:

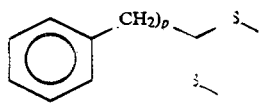

wherein p represents 0 or 1.

2. The process of claim 1 wherein p is 0.
3. The process of claim 1 wherein p is 1.
4. The process of claim 1 where the flavor augmented or enhanced is a peanut or chocolate flavor.
5. The process of claim 2 wherein the flavor augmented or enhanced is a peanut or cocoa flavor.
6. The process of claim 3 wherein the flavor augmented or enhanced is a peanut or cocoa flavor.
7. A chocolate flavor formulation containing intimately admixed therewith from about 0.1% up to about 15% by weight based on the total weight of said flavor formulation of at least one compound defined according to the structure:

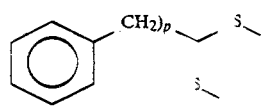

wherein p is 0 or 1.

8. A peanut flavor containing from about 0.1% to about 15% by weight based on the total weight of said flavor of at least one compound defined according to the structure:

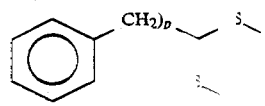

wherein p is 0 or 1.

* * * * *